United States Patent [19]

Stasz et al.

[11] Patent Number: 4,903,696
[45] Date of Patent: Feb. 27, 1990

[54] ELECTROSURGICAL GENERATOR

[75] Inventors: Peter Stasz, Moundsview, Minn.;
Scott R. Grabinger, Maple Grove, Mass.

[73] Assignee: Everest Medical Corporation, Brooklyn Center, Minn.

[21] Appl. No.: 254,203

[22] Filed: Oct. 6, 1988

[51] Int. Cl.$^4$ .............................................. A61B 17/39
[52] U.S. Cl. ........................................ 606/37; 606/39; 606/40
[58] Field of Search ...................... 128/303.13, 303.14, 128/303.17

[56] References Cited

U.S. PATENT DOCUMENTS

| | | | |
|---|---|---|---|
| 4,191,188 | 3/1980 | Belt et al. | 128/303.13 |
| 4,281,373 | 7/1981 | Mabille | 128/303.17 X |
| 4,674,498 | 6/1987 | Stasz | 128/303.14 |
| 4,727,874 | 3/1988 | Bowers et al. | 128/303.13 |
| 4,739,759 | 4/1988 | Rexroth et al. | 128/303.14 |
| 4,802,476 | 2/1989 | Norenberg et al. | 128/303.14 |

Primary Examiner—Lee S. Cohen
Attorney, Agent, or Firm—Haugen and Nikolai

[57] ABSTRACT

An electrosurgical generator for driving one or more separate electrosurgical implements, e.g., an electrosurgical scalpel and an electrosurgical forceps, over separate output channels. Bipolar electrodes on the scalpel blade are energized by a radio frequency (rf) power source which, by proper manipulation of push-button switches on the scalpel handle, can be made to operate selectively in a CUT and in a COAG (coagulate) mode. In the CUT mode, the rf energy is applied to the tissue, via electrodes which are closely spaced, yielding a high current density. In the COAG mode, the energy is applied to electrodes which are spaced relatively far apart so as to produce heating sufficient to cauterize, but not to the point where the tissue is rent. The generator also provides circuitry for energizing an ultrasonic transducer mechanically coupled to one of the surgical implements whereby vibratory energy is simultaneously applied to the implement along with the rf CUT/COAG energy. The drive to the transducer is amplitude modulated at a frequency which enhances resonance of the blade and handle containing the blade. A novel feedback control sense variations in load impedance and adjusts the power delivered to the electrodes so as to maintain a relatively flat power vs. load impedance characteristic.

8 Claims, 4 Drawing Sheets

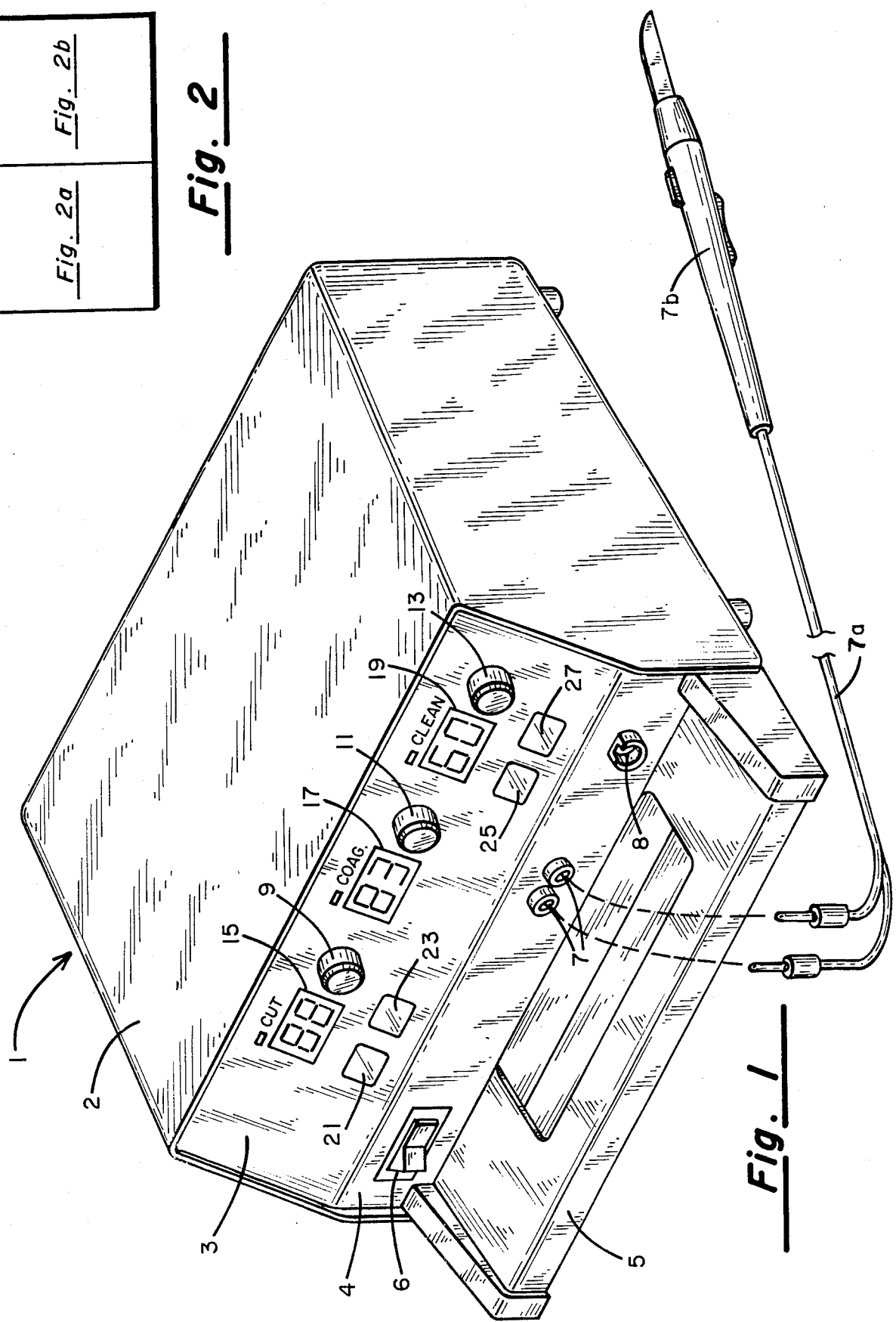

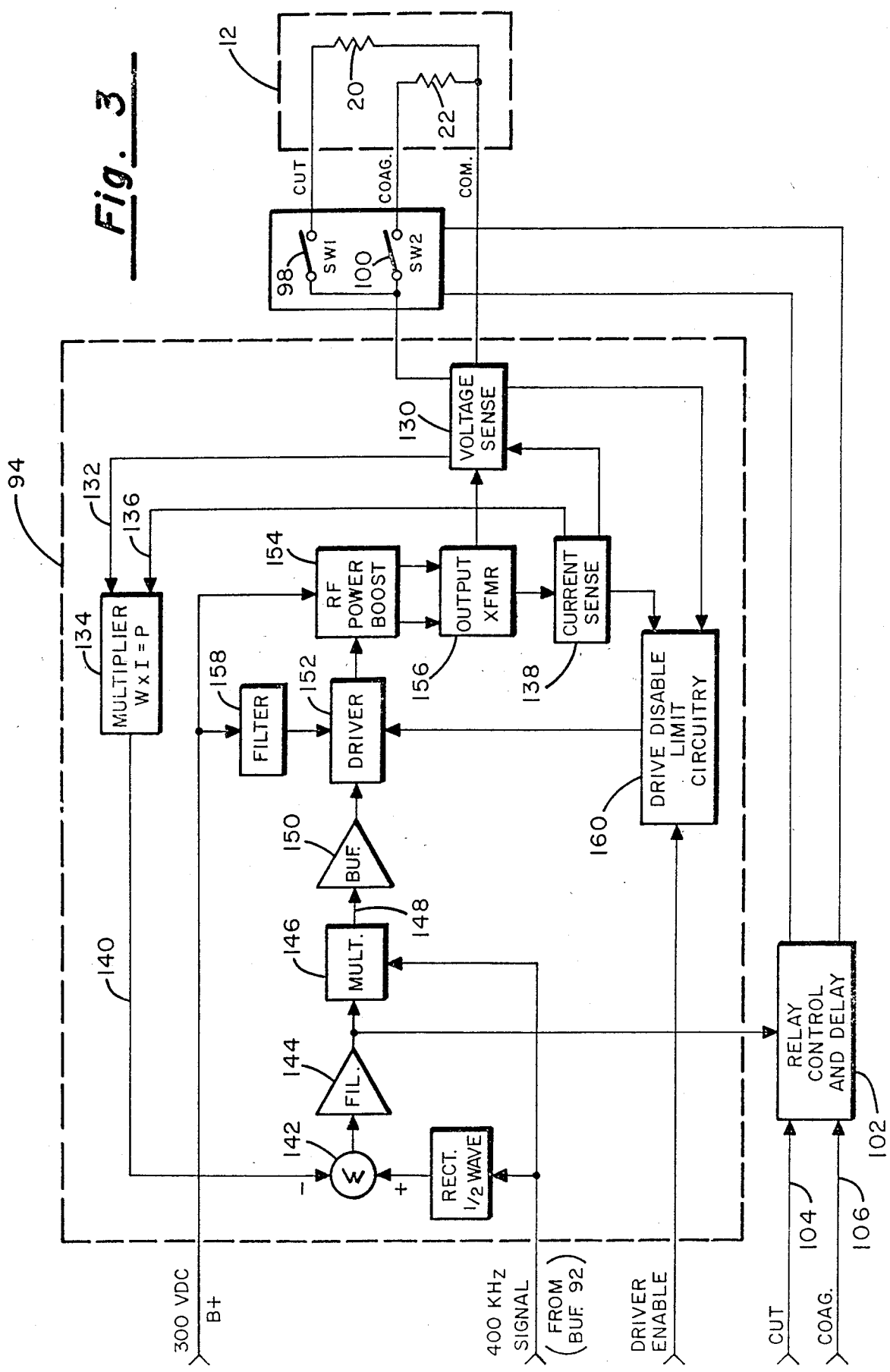

ELECTROSURGICAL GENERATOR

BACKGROUND OF THE INVENTION

I. Field of the Invention.

This invention relates generally to an electrosurgical generator having characteristics which enhance electrosurgical procedures.

II. Discussion of the Prior Art.

By now, electrosurgical procedures have become quite common and various systems are presently on the market for allowing radio frequency power to be delivered to a cutting blade, or a forceps or other implement whereby cutting of tissue or coagulation of blood can be selectively accomplished by the mere depression of appropriate control switches by the surgeon. A concise discussion of the underlying principles relating to electrosurgery is set out in the introductory portion of the Bowers U.S. Pat. No. 4,559,943, which is hereby incorporated by reference.

In the Stasz U.S. Pat. No. 4,674,498, which is assigned to applicants, assignee, there is described an electrosurgical system in which the electrosurgical blade is made to vibrate at a frequency sufficient to cause cavitation to take place as rf energy is simultaneously applied to electrodes on the blade for effecting cutting and coagulation. The high frequency vibrations of the blade have been found to markedly reduce the buildup of charred blood and tissue on the electrosurgical blade which obviates the need for frequent cleaning and/or blade replacement. The present invention is directed to an electrosurgical generator which has been specially designed to power the electrodes on electrosurgical implements while at the same time powering the transducer used to impart vibratory motion to the implement.

The electrosurgical generator of the present invention includes at least two channels, whereby more than one electrosurgical implement can be operated by a surgeon or by a surgeon and an assistant. For example, an electrosurgical scalpel of the type including a blade supported in a handle may be connected by a cable to a first channel of the generator and, by manipulating finger switches on the handle, appropriate rf energy for either cutting or coagulating may be delivered to the appropriate electrodes disposed on the scalpel blade while the blade is simultaneously vibrated. The other channel may be used in a typical situation to deliver rf energy to a bipolar forceps upon the actuation of a foot switch, also coupled to the electrosurgical generator. One or both of the implements may be simultaneously powered.

When using an electrosurgical scalpel, the impedance presented to the electrodes is found to vary depending upon the body fluids and tissue types encountered. For example, as the blade is made to pass through blood, the impedance between the blade's electrodes would be relatively low as compared to when skin and muscle tissue is encountered. Likewise, fat tissue is found to present a higher impedance than skin and muscle tissue. To avoid the necessity of frequently adjusting manual controls on the electrosurgical generator to vary the power output in accordance with the tissue being encountered, the electrosurgical generator of the present invention includes a novel feedback control network for maintaining the power output relatively flat over a wide load impedance range.

It has also been found that cleaning is enhanced where the energy used to drive the ultrasonic transducer is effectively synchronized with the rf power being delivered to the electrosurgical electrodes. Moreover, by keying the signal delivered to the ultrasonic transducer on and off at a rate which is related to the natural resonant frequency of the blade and handle combination, enhanced cleaning takes place, presumably due to an increase in the amplitude of the displacement of the vibrating blade.

The repeated switching on and off of the power being delivered to the blade in prior art electrosurgical generators has also been a rich source of electromagnet interference (EMI) which could adversely affect other electronic instrumentation found in an operating room setting. To reduce EMI, in accordance with the present invention, the turning on and off of the rf power is synchronized with the zero crossing of the rf waveform such that switching occurs when the instantaneous AC power is zero.

OBJECTS

Thus it is a principal object of the present invention to provide an improved electrosurgical generator for use with surgical implements.

Another object of the invention is to provide an electrosurgical generator for selectively applying cutting or coagulating voltages to bipolar electrodes on an electrosurgical instrument while simultaneously and synchronously driving an ultrasonic transducer for imparting vibrations to the instrument.

Yet another object of the invention is to provide an electrosurgical generator in which the power amplifier(s) utilized therein include feedback means whereby the power versus load impedance characteristics remain relatively constant over a broad range.

Still another object of the invention is to provide an electrosurgical generator for powering both bipolar electrodes and an ultrasonic transducer where the signal driving the transducer is synchronized with the rf power delivered to the electrodes and where the transducer signal is also amplitude modulated at a frequency corresponding to the natural resonance of the implement being vibrated.

A further object of the invention is to provide an electrosurgical generator which is specifically designed to minimize EMI by synchronizing the switching of the rf power with the zero crossing of the rf waveform.

SUMMARY OF THE INVENTION

The foregoing objects and features of the invention are achieved by providing an electrosurgical power supply or generator which has at least two channels, one of which utilizes a class-C amplifier as a power booster having a feedback network for simultaneously sensing load voltage and load current. The network converts signals proportional to load voltage and load current to a corresponding control voltage proportional to power which is used to adjust the peak-to-peak level of the drive applied to the power amplifier or booster. The output of the power booster is applied to the electrodes of the electrosurgical instrument through switch contacts whose on and off states are controlled by low power logic signals resulting from the closure of one or the other of the CUT and COAG switches on the hand-held implement itself.

The rf energy originates at a rf oscillator whose output is amplified and applied to a gated switch controlled by CUT and COAG control signals which are logic level signals phase-synchronized to the oscillator output. Thus, power switching occurs at the zero crossing of the rf signal. The amplitude of the power is set by power level control potentiometers which are manually adjustable by appropriate knobs on the front panel of the electrosurgical generator.

The CUT control logic signal is applied to a "Pure/Blend" control circuit which functions to provide either a 100 percent duty cycle or a factory-set duty cycle of 56 percent to a gated switch.

To drive the ultrasonic transducer, which is mechanically coupled to the electrosurgical implement, the amplified output of the aforementioned 400 KHz oscillator is fed through level setting potentiometers and a further gated switch to the input of a power amplifier whose output connects to a piezoelectric crystal. The second gated switch includes a Type 555 timer whereby the continuous wave 400 KHz signal can be keyed on and off at a desired rate and with a desired duty cycle. This allows the repetition rate of the transducer to be matched to the natural resonant frequency of the implement being vibrated for enhanced cleaning action.

The electrosurgical generator of the present invention also includes a second channel whereby another instrument, e.g., a bipolar forceps, can be energized with up to 50 watts of 400 KHz rf power. The second channel is controlled by a foot-switch which applies a reference voltage to either the CUT or the COAG inputs of the CUT/COAG control circuit. This latter circuit produces a logic signal which drives an audio alarm and a gated switch whose output is synchronized with the zero crossings of the 400 KHz output waveform. The output from the gated switch is, in turn, applied through a buffer circuit and a Class C power amplifier to the forceps. No feedback control of this amplifier is required in that the forceps load remains relatively constant. Level control potentiometers accessible to the surgeon can be used to adjust the rf power output delivered to the instrument.

DESCRIPTION OF THE DRAWINGS

The foregoing objects, features and advantages of the invention will become apparent to those skilled in the art from the following detailed description of a preferred embodiment, especially when considered in conjunction with the accompanying drawings in which:

FIG. 1 is a perspective view of the electrosurgical generator;

FIG. 3 is a further block diagram illustrating the feedback control used in conjunction with the power booster illustrated in FIG. 1.

DESCRIPTION OF THE PREFERRED EMBODIMENT

Figure 2A:
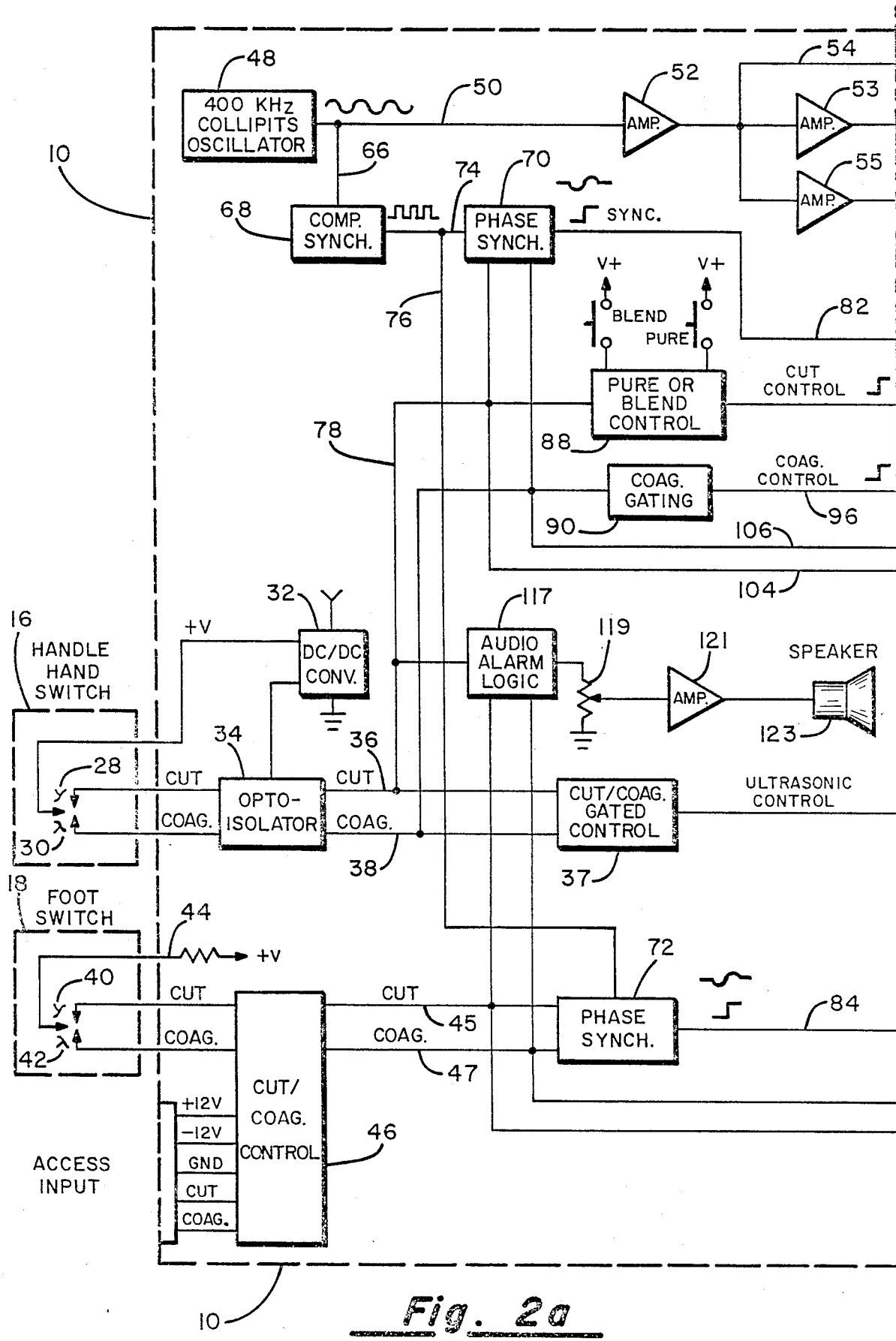
FIG. 2 is a block diagram of the electrosurgical generator in accordance with the present invention.

Referring first to FIG. 1, there is shown a perspective view of the electrosurgical generator incorporation the present invention. The generator is indicated by generally by numeral 1 and includes a box-like housing 2 with a front wall having a sloping face 3 and a vertical face 4. For convenience in carrying, a handle assembly 5 is attached to the vertical portion of the front wall as illustrated. A power on/off switch 6 is provided on the front panel as are banana plug jacks 7 which allows a cable 7a to be plugged in for linking an electrical surgical implement such as scapel 7b to the RF power outlet contained within the cabinet 2. A further outlet jack 8 permits a second electrosurgical tool or implement not shown to be coupled by a suitable cable to the generator. Three level control knobs 9, 11 and 13 are available to the operator allowing the power for cutting, coagulating and cleaning to be adjusted. A power indication is made visible in the seven-segment display windows 15, 17 and 19.

Also accessible on the sloping portion of the front panel are push-button switches 21, 23 25 and 27. Switches 21 and 23 are used to select whether the power delivered to the CUT electrodes is to be continuous wave, exhibiting a 100 percent duty cycle (pure), or pulse amplitude modulated to exhibit a lesser duty cycle (blend). The PRESET switch 25, when depressed, causes a factory preset power level to be delivered to the ultrasonic transducer used to vibrate the blade. If, on the other hand, the VARIABLE switch 27 is depressed, then rotation of the knob 13 will be effective to set the power output to the transducer.

While not shown in FIG. 1, on the back panel are jacks to which a foot switch can be connected for controlling the energization of the utensil coupled to the banana jacks 7 on the front panel.

Figure 2B:
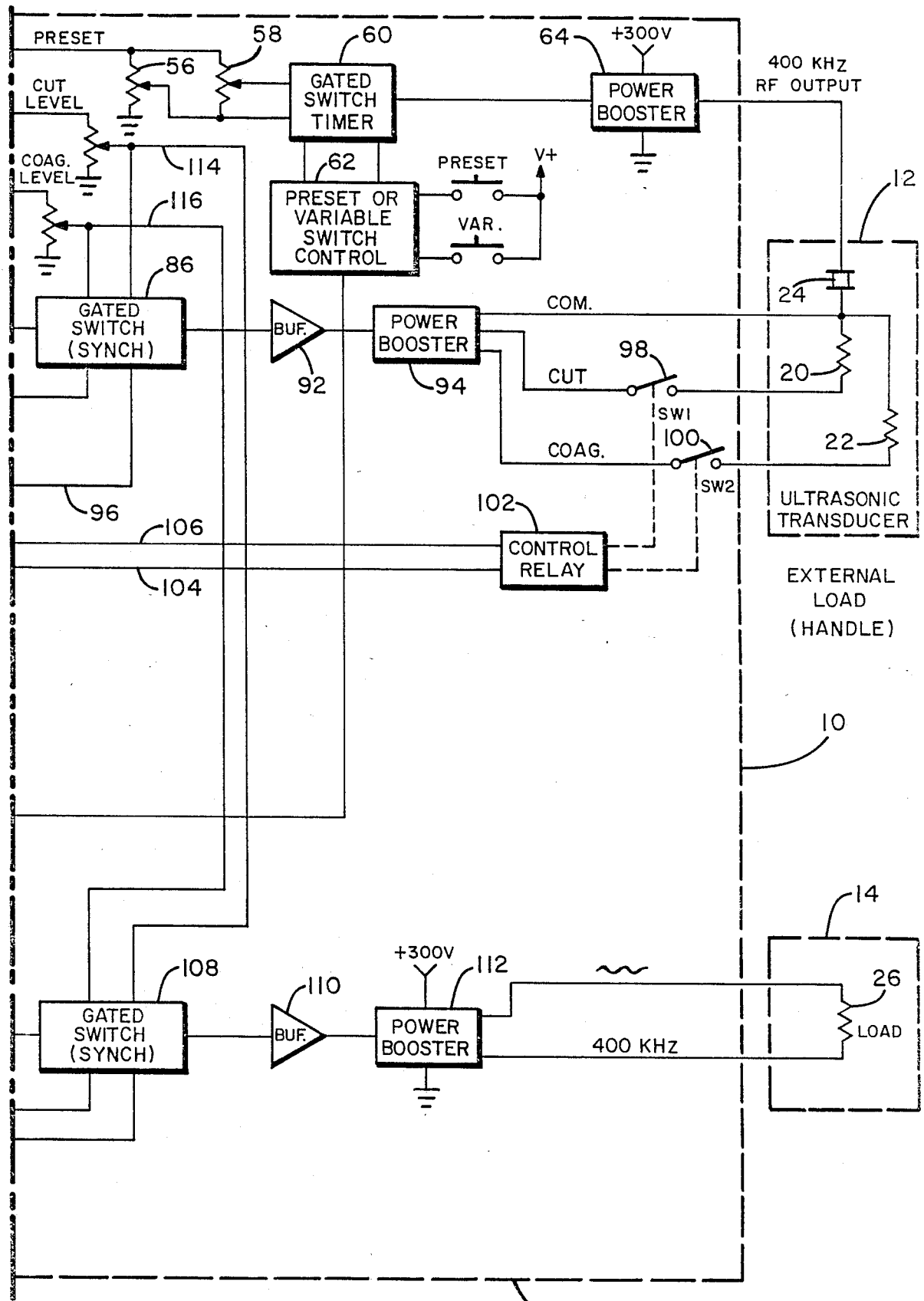

Referring to FIG. 2, there is illustrated by means of a block diagram a preferred embodiment the circuit implementation of the electrosurgical generator in accordance with the present invention. The electrosurgical generator is shown as being enclosed by the dashed lined box 10. As will be more fully explained, the electrosurgical generator includes two separate channels whereby two individual electrosurgical instruments can be simultaneously or separately controlled. For purposes of explanation, an electrosurgical scalpel, such as disclosed in application Ser. No. 56,434, filed June 1, 1987, is represented schematically by the circuitry contained within the dashed line box 12. A separate device, typically a bipolar forceps used for cauterizing ruptured blood vessels, is shown schematically within the confines of the broken line box 14. The individual controls for actuating either the electrosurgical scalpel and the bipolar forceps are shown as being enclosed by the dashed line boxes 16 and 18, respectively.

As is explained in the aforereferenced patent application, the electrosurgical scalpel includes a blade which is removably secured in a handle and a plurality of electrodes, one set for cutting and another for coagulating are suitably disposed on the blade surface. Resistors 20 and 22 represent the load impedance presented across the multiple electrodes when the scalpel is in use. Contained within the handle of the scalpel and abutting the blade is an ultrasonic transducer 24 which, as mentioned, is used to vibrate the blade at ultrasonic rates whereby when cooperating with blood and other body fluids, cavitation takes place to effectively keep the blade functional for a longer time. The load presented to the bipolar electrodes of the external forceps is represented in FIG. 1 by the resister 26 contained within the dashed line box 14.

The electrosurgical scalpel, itself, includes a pair of mode switches 28 and 30 which determine whether the blade is to operate in a CUT or a COAG mode. Specifically, when the switch 28 is closed, a positive voltage, isolated from ground, is supplied from the DC/DC converter 32 through the switch 28 to an opto-isolator 34 to provide a logic level signal on line 36 indicative that this channel is to operate in the CUT mode. If, on the other hand, the push-button switch 30 is closed, the positive voltage from the DC/DC converter 32 is applied to the opto-isolator 34, causing a logic level signal on line 38 indicative of the COAG mode. The foot switch 18 has contacts 40 and 42 which close on a mutually exclusive basis to apply a voltage from the source +V over line 44 to the CUT input of the CUT/COAG control circuit 46. If, on the other hand, switch 42 had been closed, then a COAG signal would be applied to the control circuit 46. The control circuit 46 merely serves as a buffer for producing a digital logic level pulse compatible with the CMOS circuitry used in implementing various other components of the electrosurgical generator.

Contained within the electrosurgical generator 10 is an rf oscillator 48, here shown as a 400 KHz Colpitts oscillator for producing a sinusoidal output signal on line 50. This signal is amplified at 52 and then fed over line 54 to a first level setting potentiometer 56 which is factory preset to establish a minimum threshold for the signal to be applied to the ultrasonic transducer 24 contained within the scalpel handle. A second potentiometer 58 which is available to the operator on the front panel of the generator (knob 13, FIG. 1) is used to adjust the transducer signal from the preset minimum up to a maximum corresponding to the output of the amplifier 52. The output developed across the potentiometer 58 is applied as an input to a gated switch 60 which receives its enable signal from the PRESET or VARIABLE switch control 62 (switches 25 and 27, FIG. 1). Contained within the gated switch 60 is Type 555 timer which operates to turn on and off the 400 KHz signal at a predetermined rate. As such, the 400 KHz signal is effectively amplitude modulated by a signal having a 50% duty cycle. The rate at which the signal is modulated is determined as a function of the overall resonant frequency of the blade when mounted in its blade holding handle. It could typically be in the range of from 200 Hz to 300 Hz.

The modulated signal output from the gated switch 60 is applied as an input to a Class C power amplifier 64, thus providing the requisite drive for the ultrasonic transducer 24. The PRESET or VARIABLE switch control 62 allows the user to select whether the preset level established by potentiometer 56 will be applied as an input to the power booster 64 or whether the potentiometer 58 will be included so that by manipulating knob 13 on the front panel of the electrosurgical generator, the power delivered to the transducer 24 can be varied.

The output from the 400 KHz oscillator 48 is also applied via line 66 to a comparator 68 for producing a pulse at each zero crossing of the 400 KHz sinusoidal waveform. These pulses are applied to phase synchronization circuits 70 and 72 via lines 74 and 76, respectively. The logic level signals made to appear on conductors 36 and 38 indicative of either the CUT or the COAG mode are applied via conductors 78 and 80 to the phase synchronization circuit 70. In a similar fashion, CUT and COAG logic level signals are applied to the phase synchronization circuit 72 associated with the auxiliary channel. The phase synchronization circuits 70 and 72 are effective to cause an enable signal to be generated on lines 82 and 84 whose leading edge is synchronized to the zero crossing of the sinusoidal waveform. Thus, the transition whereby the rf power is switched to the surgical implements at a point in time where the instantaneous power level is equal to zero. This has been found to greatly reduce EMI radiation through use of the electrosurgical system.

The synchronized enable signal appearing on line 82 is applied to the gated switch 86. Also applied to the gated switch 86 are the CUT control signal from PURE or BLEND control 88 and a COAG control signal from COAG gating circuit 90. The PURE control switch 21 (FIG. 1), when actuated, results in a 100 percent duty cycle waveform being applied through the gated switch 86 and the buffer amplifier 92 to a Class C power amplifier or booster circuit 94. With the BLEND switch 23 on the front panel depressed, the 400 KHz signal arriving via conductor 82 is effectively amplitude modulated so as to exhibit a predetermined duty cycle less than 100 percent, e.g., 56 percent. The enable signal on line 96 emanating from the COAG gating circuit 90 causes the gated switch 86 to output a pulse modulated 400 KHz signal having a predetermined duty cycle less than that used for cutting. Typically, a 75 percent duty cycle has been found to be useful and appropriate for the coagulating mode.

The output from the power booster 94 is applied either across the CUT electrodes or the COAG electrodes of the bipolar implement by operation of one or the other of the single pole, single throw relay contacts 98 or 100 operated by relay control 102. When the push-button 28 on the handle switches in the CUT position, a signal on line 104 causes the CUT switch 98 to close whereas if the push-button switch 30 is actuated, a signal applied over line 106 causes the relay 102 to actuate the COAG electrodes 22 via relay switch 100.

The auxiliary channel involving the foot switch 18 and the forceps implement 14 also includes a gated switch 108 which receives the 400 KHz sine wave signal from oscillator 48 via CUT level control line 114 and COAG level control line 116. Again, the gated switch is enabled by logic level signals emanating from the CUT/COAG control circuit 46 with the switching being phase synchronized by phase synchronization circuit 72, all as previously described in connection with the explanation of the phase synchronization circuit 70 in its cooperation with gated switch circuit 86.

The output from the gated switch 108 is applied via buffer 110 to a further Class C amplifier or power booster 112. The buffer 110 constitutes a driver and provides desired isolation between the input of the power amplifier 112 and the gated switch 108. The 400 KHz output from the amplifier 112 is then used to drive the auxiliary load 14. By appropriate adjustment of the CUT level by knob 9 or the COAG level by knob 11 on the front panel of the electrosurgical generator, the power delivered to the load 26 may be continuously varied between 0 and 50 watts.

To apprise the surgeon and other operating room personnel as to the operating mode then in use, an audio tone generator is also incorporated. Specifically, an audio alarm logic circuit 117 is connected to receive the CUT logic signal from switch 16 on line 36, the CUT control signal from switch 18 on line 45 and the COAG control signal from switch 16 on line 38, the COAG control signal from switch 18 on line 47 and then feeds an output, via volume control potentiometer 119 and an audio amplifier 121, to a speaker 123. The audio alarm logic 117 is configured to provide unique tone patterns from the speaker 120, depending upon which of the hand switches 28-30 or foot switches 40 or 42 are depressed. When both channels are in the CUT mode, for example, a relatively high frequency pulsed signal is generated. If only one of the switches 28 or 40 is closed, the tone will be of the same high frequency, but will be continuous rather than pulsed. Where both the COAG switch 30 and the COAG switch 42 are simultaneously closed, the audio alarm logic 117 will cause a relatively low frequency pulsed output from the speaker 123. Where only one of the switches 30 or 42 is closed, a low frequency, continuous signal is generated. When hand switch 28 and foot switch 42 are simultaneously closed or when foot switch 40 and hand switch 30 are simultaneously closed, the low and high frequency signals will alternate with an equal duty cycle. This audio signal is, of course, in addition to the visual readouts appearing on the front panel of the electrosurgical generator and serve to apprise the users of the operating state.

Having described the overall construction of mode of operation of the electrosurgical generator with the aid of FIG. 2, consideration will next be given to the feedback control utilized with the power amplifier circuit 94 whereby a relatively constant power output is maintained with changes in load impedance.

In FIG. 3, the electrosurgical blade and handle combination is again represented as being enclosed by the broken line box 12 and includes first and second sets of conductive traces on the blade which are represented by load resistors 20 and 22 with 20 being the load imposed between the CUT electrodes and 22 being the load imposed between the COAG electrodes.

A load voltage sensing circuit 130 is connected between the common electrode and the CUT and COAG electrodes on the electrosurgical scalpel by way of either switch contact 98 or 100, depending upon which is closed. Thus, the voltage sense circuit 130 senses the output voltage as seen by the load and develops a signal proportional thereto on line 132 leading to a first input of a multiplier circuit 134. The other input to the multiplier circuit is applied via conductor 136 from a load current sensing circuit 138. Thus, the signal appearing on conductor 140 connected to the output of multiplier circuit 134 is proportional to the power being drawn by the load. This power signal is fed back to one input of a summing circuit 142 whose other input is a half-wave rectified 400 KHz sine wave which serves as a reference signal. The resulting difference signal is low pass filtered at 144 and applied as a first input to a second multiplier circuit 146. The other input to the multiplier circuit 146 is, again, the 400 KHz sine wave. As a result, the signal appearing at the output of the multiplier circuit 146 on line 148 constitutes a sinusoidal signal whose peak-to-peak amplitude varies in accordance with the shifts in the DC level at the output of filter 144. This peak-to-peak signal is applied through a buffer amplifier 150 to a two-stage amplifier/driver circuit 152 and thence to a transistor power amplifier 154 forming part of the power booster 94.

The output from the Class-C rf power amplifier 154 is applied to the primary winding of an output transformer 156 whose secondary, in turn, provides the operating power to the electrosurgical implement. By using such a transformer, the electrodes $E_1$, $E_2$ and $E_3$ can be isolated from chassis ground, thus reducing the shock hazard.

The filter 158 blocks AC signals from the B+voltage utilized by the power booster 154.

The feedback controlled power booster 94 further includes a voltage/current limit circuit 160 which functions to prohibit the load current and load voltage from exceeding predetermined limits.

In operation, if load power increases, the feedback signal from the multiplier 134 to the difference circuit 142 increases, causing the output of the summing circuit to drop. This reduces the peak-to-peak swing of the 400 KHz signal delivered to the driver 152 and ultimately to the input of the power booster amplifier 154. With a reduced peak-to-peak swing, there is a corresponding drop in the power delivered to the load. Contrawise, if a drop in load power is sensed, the feedback signal from the multiplier 134 decreases, causing an increase in the peak-to-peak swing of the signal developed at the output of multiplier 146. This, then, results in an increase in the amount of power delivered by the power amplifier 154 to the load.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. Electrosurgical apparatus of the type comprising an electrosurgical blade secured in a blade supporting handle, said blade carrying a cutting electrode, a coagulating electrode and a common electrode, said handle including at least two manually operable switches for initiating the application of an RF voltage between said cutting electrode and said common electrode or between said coagulating electrode and said common electrode and an ultrasonic transducer for imparting vibrations to said blade, an improved electrosurgical generator comprising:
    (a) signal source means for producing radio frequency signals alternating in polarity about a zero voltage axis;
    (b) a first power amplifier circuit having an input terminal and a plurality of output terminal means for connection to said electrodes;
    (c) first gated switch means coupled to receive radio frequency signals from said signal source means and deliver, when enabled, said radio frequency signals to said input terminal of said first power amplifier circuit;
    (d) means associated with said two manually operable switches on said handle for selectively generating a "cut" control pulses signal and a "coag" control pulse signal, said control pulse signals having a leading and a trailing edge;
    (e) means for synchronizing the leading edge of said "cut" and "coag" control pulse signals with the crossings of said zero voltage axis by said radio frequency signals; and
    (f) means coupling the synchronized "cut" and "coag" control pulse signals to said first gated switch means for enabling said gated switch means at a time when said radio frequency signals are at a zero voltage level.

2. The apparatus as in claim 1 and further including:
    (a) a second power amplifier circuit having an input and an output, said output being connected in driving relation to said ultrasonic transducer;
    (b) a second gated switch means disposed between said signal source means and said input to said second power amplifier circuit which, when enabled, delivers said radio frequency signals to said second power amplifier circuit; and (c) means coupling said "cut" and "coag" control signals to said second gated switch means for enabling said second gated switch means.

3. The apparatus as in claim 1 or 2 wherein said first power amplifier circuit includes means for automatically adjusting the power delivered by said first power amplifier circuit to compensate for changes in impedance between said electrodes.

4. The apparatus as in claim 3 wherein said means for automatically adjusting the power delivered by said first power amplifier circuit comprises:

(a) load voltage sensing means for sensing the instantaneous load voltage developed across said electrodes and producing a first control signal proportional thereto;

(b) load current sensing means for sensing the instantaneous load current flowing through said electrodes and producing a second control signal proportional thereto;

(c) means for multiplying said first and second control signals for producing a third control signal proportional to power being delivered to a load coupled to said electrodes;

(d) means coupled to said signal source means and said means for multiplying for producing a fourth control signal, the peak-to-peak amplitude of which varies as a function of said third control signal; and (e) means for applying said fourth control signal as the input to said first power amplifier circuit.

5. The apparatus as in claim 4 wherein said means for automatically adjusting the power delivered by said first power amplifier circuit further includes:

(a) means coupled to said first power amplifier circuit and to said load voltage sensing means and said load current sensing means for limiting the power delivered to a load connected between said electrodes to a value less than a predetermined maximum.

6. The apparatus as in claim 2 and further including means for amplitude modulating the signal applied as an input to said second power amplifier circuit with a signal having a predetermined modulating frequency.

7. The apparatus as in claim 6 wherein the modulating frequency is related to the resonant frequency of said blade and handle.

8. The apparatus as in claim 6 and further including means for manually adjusting the amplitude of said radio frequency signal applied to said second gated switch means.

* * * * *